United States Patent [19]

Tucker

[11] Patent Number: 5,050,598
[45] Date of Patent: Sep. 24, 1991

[54] BODY WARMING BLADDER

[76] Inventor: Dalton R. Tucker, 18218 Paradise Mountain Rd., No. 91, Valley Center, Calif. 92082

[21] Appl. No.: 432,550

[22] Filed: Nov. 7, 1989

[51] Int. Cl.⁵ .............................................. A61F 7/08
[52] U.S. Cl. .................... 128/403; 383/401; 128/382; 446/74; 36/2.6
[58] Field of Search ............... 383/901; 128/399, 400, 128/402, 382, 403; 446/74; 62/530; 2/158; 126/204, 263; 206/219; 36/2.6

[56] References Cited

U.S. PATENT DOCUMENTS

| | | | |
|---|---|---|---|
| D. 116,004 | 8/1939 | Albright | 383/901 |
| 551,939 | 12/1895 | Weber | 128/403 |
| 853,639 | 5/1907 | Hincks | 383/901 |
| 1,396,176 | 7/1920 | Chambers | 446/74 |
| 1,522,295 | 1/1925 | Gee | 128/402 |
| 1,937,387 | 11/1933 | Kilcup | 383/901 |
| 1,970,081 | 8/1934 | Eisendrath | 2/158 |
| 2,675,798 | 4/1954 | Rosmarin | 126/204 |
| 3,175,558 | 4/1954 | Calliouette et al. | 128/403 |
| 3,780,537 | 12/1973 | Spencer | 62/530 |
| 3,804,077 | 4/1974 | Williams | 126/263 |
| 3,874,504 | 4/1975 | Verakas | 206/219 |
| 4,204,110 | 5/1980 | Smit et al. | 128/399 |
| 4,249,319 | 2/1981 | Yoshida | 36/2.6 |
| 4,441,483 | 4/1984 | Cieslak et al. | 126/206 |
| 4,516,564 | 5/1985 | Koiso et al. | 126/263 |
| 4,714,445 | 12/1987 | Templeton | 446/74 |
| 4,756,564 | 5/1985 | Francis, Jr. | 128/403 |
| 4,759,084 | 7/1988 | Madnick et al. | 2/158 |
| 4,783,866 | 11/1988 | Simmons et al. | 128/403 |
| 4,816,000 | 3/1989 | Hsu | 383/901 |

*Primary Examiner*—Edward M. Coven
*Assistant Examiner*—Mark S. Graham
*Attorney, Agent, or Firm*—Brown, Martin, Haller & McClain

[57] ABSTRACT

A body warming bladder of pliable, waterproof material has a central portion and at least two separate limbs. The bladder has an opening for filling it with heated liquid, and a releasable end cap for normally sealing the opening. In one version of the invention the bladder is shaped to correspond substantially to the shape of a child's plush toy and is mounted inside the body of the toy with a portion of the bladder extending up to a suitable access opening in the body which registers with the bladder opening to allow the bladder to be filled with warm water. In another version the bladder is of generally V- or boomerang like shape with the access opening at the center of the V-shape, and can be fitted inside a slipper to warm the wearer's feet or used to warm other body parts.

9 Claims, 1 Drawing Sheet

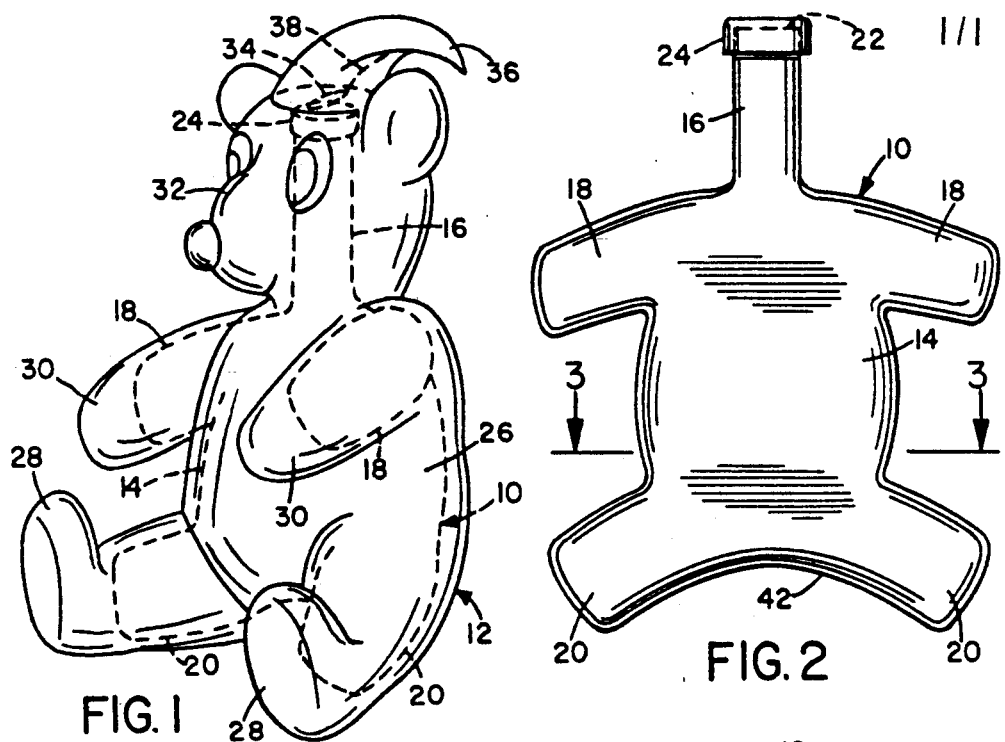
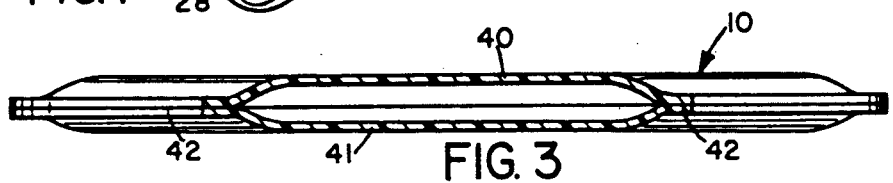
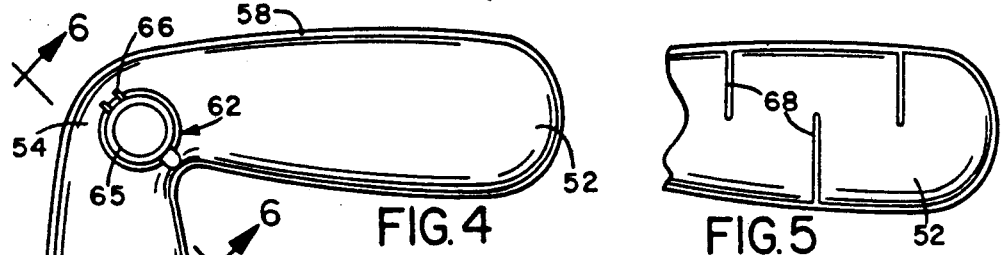
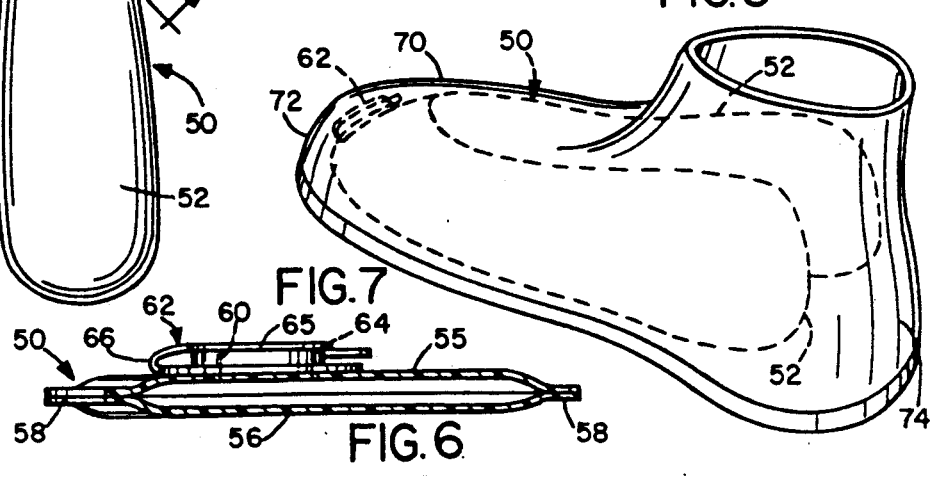

BODY WARMING BLADDER

BACKGROUND OF THE INVENTION

The present invention relates generally to a body warming bladder for containing a heated liquid to provide warmth to a user's body.

Known hot water bottles of relatively thick rubber or like materials are generally of a flat, rectangular shape and do not conform easily to the shape of parts of the body to be warmed, such as the feet, for example. Thus, typically, only a relatively small area is actually in contact with the bottle at any one time. Also, they are only suitable for using in one place and cannot easily be carried around during everyday activities. Water beds can be heated, but are typically relatively expensive and have other disadvantages.

SUMMARY OF THE INVENTION

It is an object of the present invention to provide an improved body warming bladder.

According to the present invention, a body warming device is provided which comprises a bladder or outer container of pliable, waterproof material having a shape including a central region and at least two separate limbs extending from the central region, the container having an inlet/outlet opening for filling it with a hot or warm liquid and subsequently emptying it after use, and an end cap for releasably sealing the inlet/outlet opening.

In one embodiment of the invention, the bladder is shaped to fit inside the body of a plush toy such as a teddy bear, the shape comprising a body portion, limb portions, and a neck portion. The fill opening is preferably provided at the end of one of the extremities, and in the preferred embodiment of the invention the neck is extended to project up to the top of the head of the toy and has a fill opening at its end. The head of the toy is provided with an access opening aligned with the fill opening for access to the fill opening, and the end cap comprises a suitable child proof or child resistant closure such as the type used on medicine bottles or other containers of materials potentially harmful to children. The bladder fits permanently inside the toy with the end cap being accessible through the opening provided for that purpose in the outer body wall of the toy. The opening may be normally concealed by means of clothing, for example a night cap having a slit-like opening for access to the end cap for emptying and refilling purposes. Alternatively, the access opening may have an in-built fastener such as a zipper or the like so that the opening may be closed while the toy is in use.

This embodiment results in a cuddly toy with a warm body, which will have great appeal to children, who normally like to hug a cuddly toy in bed and will therefore be warmed by the internal bladder filled with hot or warm water, which in turn warms the body of the toy. The bladder can be emptied when cold and refilled by an adult quickly and easily via the child proof end cap, which can normally be concealed by or closed by fasteners or suitable clothing on the toy such as a bedcap. A toy such as a teddy bear is often carried around by children during the day as well as being held in bed, resulting in a body warming device which can conveniently provide warmth at all times.

According to another embodiment of the present invention, the bladder or container has a V-shaped outline, for fitting inside slippers or other types of loose fitting footwear to warm the feet when filled with warm water. Preferably, an inlet opening is provided at the corner or center of the V-shape and a suitable releasable closure cap normally closes the opening. In use, the bladder fits over the periphery of the foot on the inner, angled end of the V-shape shape fitting over the toes and the opposite arms of the V-shape fitting around the opposite sides of the foot. Preferably, the arms are long enough to extend up to or close to the heel region. The bladder is held in position by the overlying slipper or other footwear. This will aid in keeping the feet warm. Since the extremities of the body such as the feet typically lose heat faster than other regions, use of the foot warming bladders will be helpful in providing a comfortable body temperature. The bladder may also be used in other regions if desired, such as around the neck or over the shoulders.

BRIEF DESCRIPTION OF THE DRAWINGS

The present invention will be better understood from the following detailed description of some preferred embodiments, taken in conjunction with the accompanying drawings, in which like reference numerals refer to like parts, and in which:

FIG. 1 illustrates a typical stuffed animal incorporating the body warming bladder according to a first embodiment of the invention;

FIG. 2 is a front elevation view of the bladder shaped to fit the stuffed animal;

FIG. 3 is an enlarged sectional view taken on line 3—3 of FIG. 2;

FIG. 4 is a side elevation view of an alternative configuration of the bladder according to a second embodiment of the invention;

FIG. 5 illustrates a portion of FIG. 4 with optional anti-slosh baffles;

FIG. 6 is an enlarged sectional view taken on line 6—6 of FIG. 4; and

FIG. 7 illustrates one possible use of the bladder in FIG. 4 in a slipper.

DESCRIPTION OF THE PREFERRED EMBODIMENTS

FIGS. 1 to 3 of the drawings illustrate a first embodiment of a body warming bladder 10 according to the present invention. In this embodiment, the bladder is shaped to conform to the general outline of a cuddly or plush children's toy such as a teddy bear 12 as illustrated in FIG. 1. As best illustrated in FIG. 2, the bladder 10 has a central body region 14, an elongated neck portion 16, a pair of arms 18 and a pair of legs 20. The neck portion 16 has an inlet/outlet opening 22 at its free end and a releasable closure cap assembly 24 of a twist on, childproof type is mounted on the neck opening 22. The childproof or child resistant cap assembly is of the type well known for securing medical bottles or other containers of potentially hazardous materials to reduce the risk of children removing the caps. Such cap assemblies generally require some dexterity and manipulation for separating the cap from the neck of the container, for example pushing down on the cap while twisting in order to engage the threads, which is normally beyond the capability of a small child. Such assemblies are of a well known nature and will therefore not be described in any more detail here.

The bladder 10 is permanently mounted inside the body 26 of a toy such as teddy bear 12, as illustrated in FIG. 1. Suitable padding material will be provided in regions of the body into which the bladder does not extend, for example the ends of the feet 28 and arms 30, and the outer extremities of the head 32. The neck extends up to the top of the head of the bear with its normally capped fill opening 22 aligned with a suitable access opening 34 provided in the top of the bear's head. The capped end of the neck may extend slightly upwards through the opening 34 for easy access. Preferably, the opening 34 is normally concealed by clothing such as a night cap 36 which is suitably sewn onto the head of the bear and has a suitable slit 38 for access to the opening. Alternatively, access opening 34 may have a releasable closure such as a zipper to normally conceal the end cap 22.

The bladder is made from any suitable pliable waterproof material, such as relatively thin, lightweight Latex or 16 gauge vinyl material. Preferably, a sheet of the material is cut to form two panels 40,41 of corresponding or matching outline, and the panels are laid one on top of the other with the peripheral edges 42 apart from the neck opening being suitably sealed together by heat sealing or by means of a suitable adhesive bonding agent. The childproof cap assembly 24 will be suitably bonded to the neck opening. The cap assembly will be in two parts, comprising a neck or sleeve part for securing to the neck opening of the bladder, and a releasable cap for releasable mating engagement over the sleeve part.

In use, a child's parent or other adult will fill the bladder with warm or hot water via the neck opening, and then close and seal the opening with the child proof cap. This results in an appealing cuddly toy which has the added benefit of being warm due to the internal heated bladder, and can keep a child warm at night or at any time when the weather is cold. When the water becomes cool, the adult simply removes the cap via the access openings in the night cap and bear's head, empties the water from the bladder, and refills the bladder with warm water if desired. The fill opening may be provided at the end of an arm or leg instead of the neck, if desired, with suitable access openings provided in one of the bear's arms or feet which may be covered by a glove or sock, for example.

Although the illustrated bladder is designed to fit inside a toy teddy bear, alternative bladder shapes may be made for fitting inside other plush toy animals and the like, the bladders being designed to substantially fill the body cavity of the toy animal and to extend at least partway into the limbs and head regions.

FIGS. 4 to 6 illustrate a bladder 50 according to another embodiment of the invention. In this embodiment, the bladder is of V or boomerang-like shape, having a pair of limbs 52 extending from the center or angle 54 of the V-shape. The angle of the V or boomerang is preferably around 90 degrees. As in the previous embodiment, the bladder 50 is preferably formed from two sheets 58,56 of a suitable, pliable waterproof material such as latex or vinyl, each cut out to the desired matching, V-shaped contour, and secured together around their peripheral edges 58 by heat sealing or suitable adhesive bonding material.

One of the sheets or panels 55 has a fill opening 60 located at the center or angle 54 of the V-shape, and a suitable closure cap assembly 62 is secured over opening 54, as best illustrated in FIGS. 4 and 6. The cap assembly may be of any known screw or push on type, and in the embodiment illustrated comprises a sleeve portion 64 suitably bonded to opening 60 and a push on cap 65 for releasable sealing engagement in sleeve portion 64. The cap is secured to the sleeve portion via connecting webs 66 in a known manner to reduce the risk of loss. Similar connecting webs are preferably provided on the child proof closure assembly of the first embodiment of the invention.

Internal baffles 68 as illustrated in FIG. 5 may be provided in each of the limbs of the bladder if desired. As illustrated, the baffles 64 extend transversely partway across the limb alternately from opposite sides of the limb to produce a generally serpentine path for liquid filling the limb. The baffles may be formed integrally with one of the sheets or panels of the bladder by molding or the like, and may be suitably bonded to the opposing panel of the bladder during manufacture. The baffles are optional and may be used if desired to restrict sloshing movement of the liquid in the bladder.

The body warming bladder of FIGS. 4 to 6 may be used in various ways, but one preferred use to which it is particularly suited is illustrated in FIG. 7. Prior to use, the bladder will be filled with warm or hot water. FIG. 7 illustrates the bladder fitted inside a slipper or similar piece of footwear 70 with the center or angled portion at the toe region 72 while the opposite limbs extend rearwardly towards the heel 74 along opposite sides of the slipper. The bladder will therefore enclose a major portion of a person's foot in the slipper and will keep the foot warm. Since extremities such as feet typically become cold faster than other body regions, the use of bladders 50 in each slipper will provide comfort and warmth in cold conditions. Bladders may be provided in a range of sizes to fit different size feet, for example from children's shoe sizes up to the largest adult sizes. The bladder may be installed in the lining of the slipper, if desired, with a suitable access opening in the toe region, for example, the opening being normally closed by a cover flap or the like.

Although the bladder is illustrated as used in a slipper or the like, it may be used to warm other body parts such as the neck or shoulder regions, for example by inserting it in a sock or a scarf and draping it around the neck or over the shoulders.

The body warming device or bladder of this invention is inexpensive and convenient to use both during the day and when in bed.

Although some preferred embodiments of the invention have been described above by way of example only, it will be understood by those skilled in the field that modifications may be made to the disclosed embodiments without departing from the scope of the invention, which is defined by the appended claims.

I claim:

1. A body warming bladder device for fitting over a foot inside a slipper or other footwear, comprising:

a hollow bladder of pliable, waterproof material comprising upper and lower layers having peripheral edges of matching shape, the layers being joined together around their peripheral edges to define a cavity and the bladder being of V-shape having a central, apex portion and two separate limbs extending from the central portion and diverging away from one another to form the V-shape with the limbs being unconnected and separate from one another along their length between the apex of the V-shape and the outermost free ends of the limbs;

the bladder having an inlet/outlet opening in one of said layers spaced from said peripheral edges for filling the bladder with warm liquid and subsequently emptying the bladder; and releasable end cap means for releasably sealing the inlet/outlet opening.

2. The device as claimed in claim 1, wherein the end cap means comprises a sleeve part secured to the inlet/outlet opening and a closure cap for releasable mating engagement with the sleeve part.

3. The device as claimed in claim 1, wherein the fill opening is located in the central, apex portion of the upper layer of the bladder.

4. The device as claimed in claim 1, wherein the V-shape has a 90 degree angle.

5. The device as claimed in claim 1, wherein the material is a 16 gauge plastics material.

6. The device as claimed in claim 1, wherein the material is vinyl.

7. The device as claimed in claim 1, wherein the material is latex.

8. A body warming plush toy device, comprising:
 a hollow outer body having a torso, a pair of upper limbs, a pair of lower limbs, and a head;
 an internal hollow bladder of pliable waterproof material within the outer body, the bladder having a torso portion substantially filling the torso of the outer body, a pair of upper limbs extending partially along the length of the respective upper limbs of the outer body, a pair of lower limbs extending partially along the length of the respective lower limbs of the outer body, and an elongated, straight neck portion of uniform diameter extending from a central region in an upper end of the torso portion through the head of the outer body to a location adjacent a top portion of the head;
 the hollow outer body containing padding material at the outer ends of each limb into which the bladder limbs do not extend, and in the head to fill the area surrounding the neck portion of the bladder;
 the outer body having an access opening at the top portion of the head adjacent an upper end of said elongated neck portion;
 the upper end of said elongated neck portion having a fill opening aligned with said access opening; and
 releasable end cap means for releasably sealing the fill opening.

9. The device as claimed in claim 8 including a hat secured to the head portion covering the access opening, the hat having a slit for access to the access opening.

* * * * *

UNITED STATES PATENT AND TRADEMARK OFFICE
Certificate

Patent No.: 5,050,598

Patented: Sept. 24, 1991

On petition requesting issuance of a certificate of correction of inventorship pursuant to 35 U.S.C. 116, it has been found that the above-identified patent, through error and without deceptive intent, improperly sets forth the inventorship. Accordingly, it is hereby certified that the correct inventorship of this patent is: Dalton R. Tucker, Valley Center, Calif., and Gary E. Kaeter, Chula Vista, Calif.

Signed and Sealed this Twelfth-Day of November, 1991.

EDWARD M. COVEN

*Supervisory Patent Examiner*
*Group 330*